United States Patent [19]
Webster, Jr.

[11] Patent Number: 6,066,125
[45] Date of Patent: May 23, 2000

[54] OMNI-DIRECTIONAL STEERABLE CATHETER

[75] Inventor: Wilton W. Webster, Jr., Baldwin Park, Calif.

[73] Assignee: Cordis Webster, Inc., Baldwin Park, Calif.

[21] Appl. No.: 09/190,385

[22] Filed: Nov. 10, 1998

Related U.S. Application Data

[62] Division of application No. 08/924,611, Sep. 5, 1997.

[51] Int. Cl.$^7$ .......................... A61M 25/01; A61M 37/00
[52] U.S. Cl. ............................................ 604/528; 604/95
[58] Field of Search .................... 604/95, 264, 523, 604/528, 533, 538; 607/115, 116, 122; 128/772, 642, 656.8; 606/46, 129, 41

[56] References Cited

U.S. PATENT DOCUMENTS

| | | | |
|---|---|---|---|
| Re. 34,502 | 1/1994 | Webster, Jr. ............................. | 607/125 |
| 3,470,876 | 10/1969 | Barchilon ................................ | 128/348 |
| 3,605,725 | 9/1971 | Bentov .................................. | 128/2.05 R |
| 3,625,200 | 12/1971 | Muller ................................... | 128/2.05 R |
| 4,191,196 | 3/1980 | Bradley et al. ......................... | 128/733 |
| 4,233,991 | 11/1980 | Bradley et al. ......................... | 128/733 |
| 4,685,457 | 8/1987 | Donenfeld ............................. | 128/207.14 |
| 4,753,223 | 6/1988 | Bremer .................................. | 128/4 |
| 4,826,087 | 5/1989 | Chinery ................................. | 239/551 |
| 4,838,859 | 6/1989 | Strassmann ............................ | 604/95 |
| 4,921,482 | 5/1990 | Hammerslag et al. .................. | 604/95 |
| 4,960,134 | 10/1990 | Webster, Jr. ........................... | 128/786 |
| 4,998,916 | 3/1991 | Hammerslag et al. .................. | 604/95 |
| 5,019,090 | 5/1991 | Pinchuk ................................ | 606/194 |
| 5,037,391 | 8/1991 | Hammerslag et al. .................. | 604/95 |
| 5,108,368 | 4/1992 | Hammerslag et al. .................. | 604/95 |
| 5,318,525 | 6/1994 | West et al. ............................. | 604/95 |
| 5,325,845 | 7/1994 | Adair .................................... | 604/95 X |
| 5,334,145 | 8/1994 | Lundquist et al. ..................... | 604/95 |
| 5,368,564 | 11/1994 | Savage .................................. | 604/95 |
| 5,383,923 | 1/1995 | Webster, Jr. ........................... | 607/125 |
| 5,397,304 | 3/1995 | Truckai ................................. | 604/95 |
| 5,397,321 | 3/1995 | Houser et al. ......................... | 606/41 |
| 5,419,767 | 5/1995 | Eggers et al. .......................... | 604/114 |
| 5,431,168 | 7/1995 | Webster, Jr. ........................... | 128/658 |
| 5,441,483 | 8/1995 | Avitall .................................. | 604/95 |
| 5,456,664 | 10/1995 | Heinzelman et al. ................... | 604/95 |
| 5,492,119 | 2/1996 | Abrams ................................. | 128/642 |
| 5,507,725 | 4/1996 | Savage et al. ......................... | 604/95 |
| 5,588,964 | 12/1996 | Imran et al. ........................... | 604/95 |
| 5,626,136 | 5/1997 | Webster et al. ........................ | 128/642 |
| 5,656,029 | 8/1997 | Imran et al. ........................... | 604/95 |
| 5,656,030 | 8/1997 | Hunjan et al. ......................... | 604/95 |
| 5,681,280 | 10/1997 | Rusk et al. ............................ | 604/95 |
| 5,848,986 | 12/1998 | Lundquist et al. ..................... | 604/22 |

*Primary Examiner*—Ronald Stright
*Assistant Examiner*—Patricia M. Bianco
*Attorney, Agent, or Firm*—Christie, Parker & Hale, LLP

[57] ABSTRACT

A multi-directional electrode catheter comprising an elongated tubular catheter body, a catheter tip section at the distal end of the catheter body and a control handle at the proximal end of the catheter. The catheter body may have a central lumen, and four off-axis lumens symmetrically positioned about the central lumen. A puller wire extends from the central handle through each off-axis lumen and is anchored to the tip section at a selected location. Within each off-axis lumen in the catheter body, there is provided a compression coil in surrounding relation to the puller wire. The compression coil is fixedly attached to the catheter body at its distal and proximal ends. At its proximal end, each puller wire is attached to a movable piston in the control handle. Moreover, each piston is controlled by an operator using a slidable button fixedly attached to each piston. Movement of a selected button results in movement of a selected puller wire and deflection of the tip section in the direction that puller wire.

13 Claims, 8 Drawing Sheets

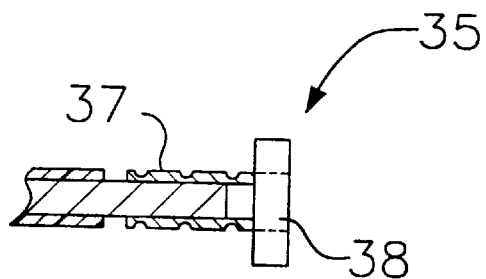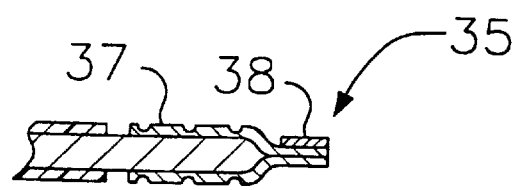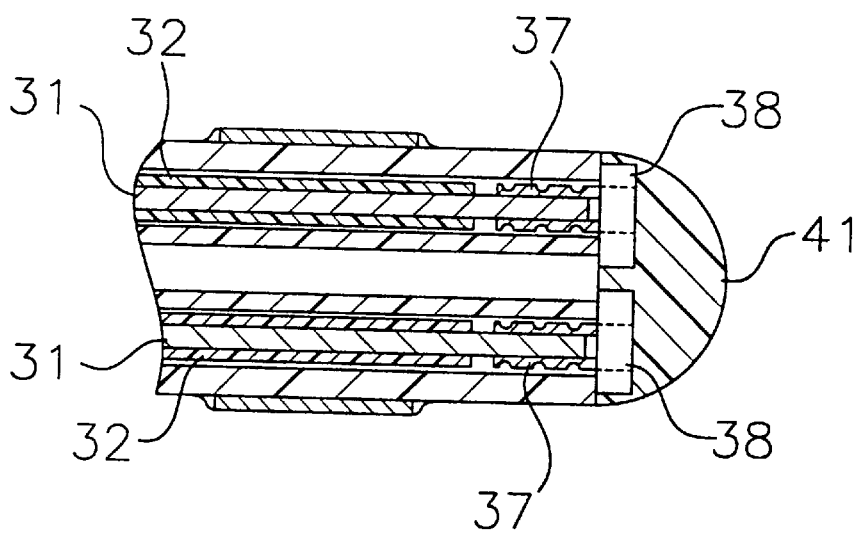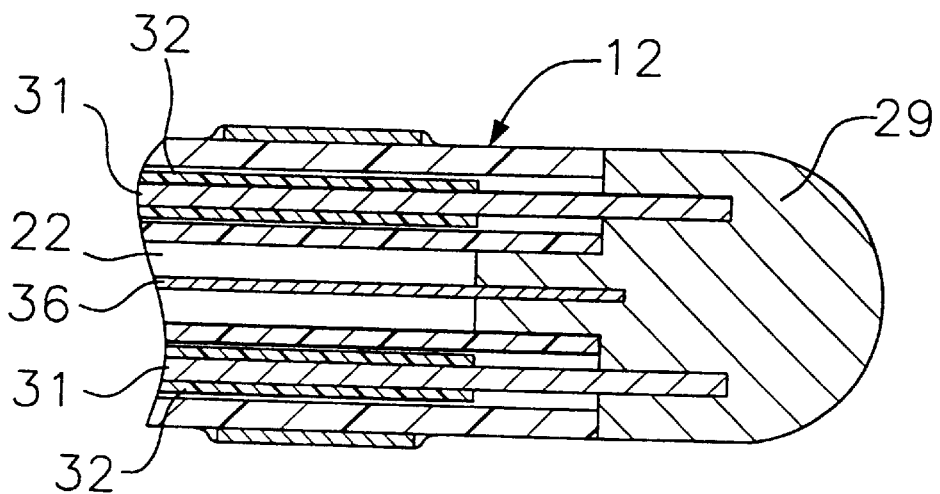

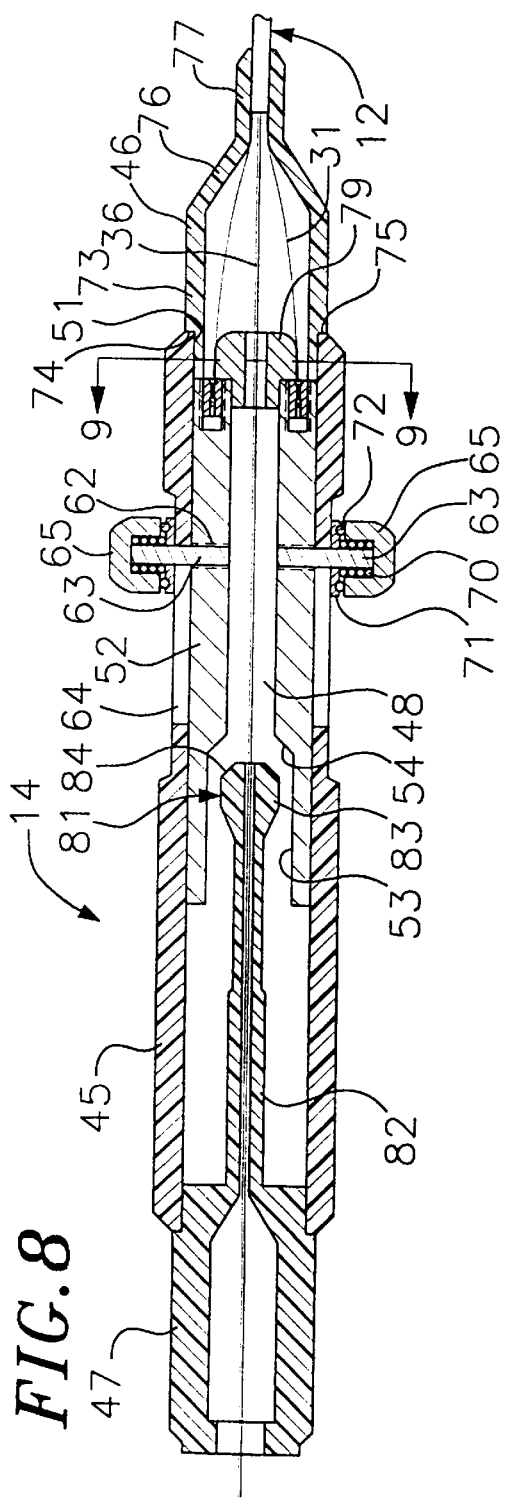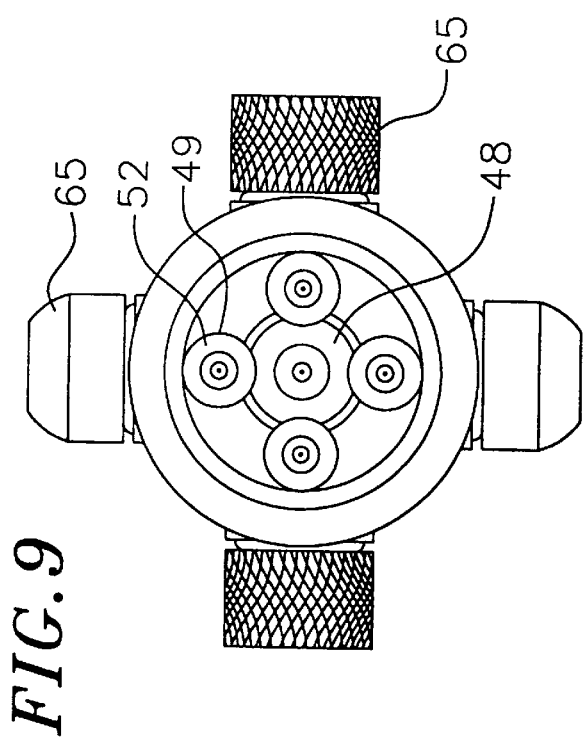
FIG.8
FIG.9

OMNI-DIRECTIONAL STEERABLE CATHETER

This application is a divisional of U.S. patent application Ser. No. 08/924,611, filed Sep. 5, 1997.

FIELD OF THE INVENTION

This invention relates to catheters having steerable tips and particularly to a catheter having a tip which is steerable in multiple directions.

BACKGROUND OF THE INVENTION

Steerable or deflectable tip cardiovascular catheters are useful in many applications, being a marked improvement over catheters with fixed tip curves. They are especially useful in the field of electrophysiology for performing radio frequency ablation of abnormal electrical pathways in the heart.

There are presently several usefull designs of steerable tip catheters. One such steerable tip catheter is described in Reissue Pat. No. 34,502. The catheter has an elongated catheter body and tip portion which can be deflected into a semi-circle in one direction. In addition, the catheter body and tip portion can be rotated. Therefore by tip deflection, catheter rotation and catheter translation, i.e., lengthwise movement of the catheter, contact of the tip portion with most areas of a heart chamber may be made.

There are, however, structures and irregularity in the heart chambers which often make access difficult. In some cases it is necessary to reach around obstacles to contact a desired site. Moreover, it may be necessary to use a longer or shorter deflectable tip portion to reach a particular site and maintain adequate stable contact.

One early multidirectional deflectable tip catheter had a catheter body and tip with 5 lumens, i.e., a central lumen and four outer lumens disposed symmetrically around the central lumen. This catheter had four puller wires which extended through the outer lumens. The distal ends of the puller wires were attached to a ring at the tip and the proximal ends were attached to a "joy stick". The central lumen was open at its distal end and connected to a luer hub at its proximal end. This catheter had no reinforcement in its body or tip. It was not suitable for electrophysiology because it had effectively no torque transmission to the tip which made tip rotation difficult. Moreover, the catheter body was subject to the same deflection as the tip, but to a lesser degree.

A more recent steerable catheter has a steerable tip that is controlled by a bendable control handle. Multiple puller wires connect the steerable tip to this control handle which can be bent in any direction and can be thought of as a multiple ball joint with friction. The tip, once deflected, can be further deflected laterally by an internal stylette. The disadvantage of this catheter design is that the tip is very soft and has poor lateral stiffness due to the presence of the stylette which cannot transmit torque effectively. Because of this, an electrode at the tip of the catheter cannot be held firmly against the myocardial wall.

Another recent steerable tip catheter comprises a deflectable tip which can be deflected in one direction by a puller wire and further deflected laterally by an internal stylette. The stylette can also be moved axially within the catheter to change the shape of the tip curvature. The disadvantage of this catheter design is that the lateral stiffness of the tip is dependent upon the stylette which cannot transmit torque effectively.

In a design wherein the tip is rotated by means of a stylette, it follows that the lateral stiffness of the tip must be less than that of the stylette alone. This is because some torque from the stylette is required to rotate the tip. Moreover, the stylette must be kept small to allow the catheter body and tip to bend and to be safe within the patient body and heart.

SUMMARY OF THE INVENTION

The present invention provides a cardiovascular catheter comprising a steerable catheter tip section, an elongated catheter body and a control handle. The catheter tip section comprises at least two and preferably four off-axis lumens. The catheter body comprises at least one lumen in communication with the off-axis lumens of the catheter tip section. Preferably, the catheter body comprises a single lumen in communication with four off-axis lumens in the catheter tip section. In an alternately preferred embodiment, the catheter body comprise separate off-axis lumen aligned with each off-axis lumen of the catheter tip section. The control handle which is attached to the proximal end of the catheter body, comprises a separate movable, preferably slidable, member associated with each of the off-axis lumens of the catheter tip section.

An elongated puller wire is connected at its proximal end to each of the movable members of the control handle. Each puller wire extends through a lumen of the catheter body into the off-axis lumen in the catheter tip section and is anchored at its distal end to the wall of the catheter tip section or to a tip electrode. Movement of a movable member in the control handle results in movement of the puller wire connected to that movable member in a proximal direction relative to the catheter body and deflection of the tip section in the direction of the moved puller wire.

Preferably, the movable members are slidable within the control handle. An elongated puller wire is attached at the proximal end to each of the slidable members in the control handle. Each puller wire extends through a lumen in the catheter body into an off axis lumen in the catheter tip section and is anchored either in the lumen wall or in a tip electrode. Proximal movement of a slidable member results in proximal movement of its puller wire relative to the catheter body and deflection of the catheter tip in that off axis direction.

Means are preferably provided for resisting compression forces on the catheter body when a puller wire is moved in a proximal direction relative to the catheter body. Preferred means comprise a compression coil which extends through the catheter body in surrounding relation to each puller wire. The proximal end of the compression coil is fixedly attached to the proximal end of the catheter body and the distal end of the compression coil is fixedly attached to the distal end of the catheter body and/or at a selected location along the length of the catheter tip section. The site of the distal attachment of the compression coil and the anchor site of the puller wire associated with that compression coil in the tip section determine the length of the tip deflection curvature in the direction of that puller wire.

In a preferred embodiment of the invention, the catheter body and tip section contain four lumens arranged symmetrically in quadrants through which four puller wires extend. Each puller wire extends through a separate lumen from the control handle through the catheter body to an anchor site in the tip section. Within the catheter body, each lumen contains a compression coil in surrounding relation to the puller wire for resisting the compressive force of the puller wire, thereby preventing deflection of the catheter body. The compression coil is fixedly attached to the proximal end of the catheter body and also near the transition of the catheter body to the tip section.

In a particularly preferred embodiment of the invention, the puller wires are separated into first and second pairs, each pair containing diametrically opposed puller wires. The anchor sites of the first pair of puller wires in the tip section are more proximal to the distal end of the tip section than the anchor sites of the second pair. In this arrangement, proximal movement of a puller wire from the first pair results in a first curve of the proximal portion of the catheter tip in the direction of the quadrant of that puller wire generally in a plane containing the axis of the catheter body. Thereafter, proximal movement of an adjacent puller wire of the second pair results in a second, more distal curve in the direction of that adjacent puller wire quadrant in a plane generally transverse to the axis of the catheter body. Such a compound curve is particularly useful in reaching around obstructions such as a papillary muscle or chorda within the heart In a preferred embodiment of the invention, there is provided a fifth lumen located central to the four quadrant lumens. The fifth lumen runs the full length of the catheter body and tip section, or the full length of the tip section alone in a preferred embodiment. In an electrophysiology catheter, the fifth lumen may serve to carry the electrode lead wires. In other instances the fifth lumen may be open at its distal end to conduct fluids into or out of the vascular system. It may also serve to conduct other energy delivery devices such as an optical fiber, to carry a fiber optic bundle for direct viewing, to inflate a balloon, to serve as a conduit for needles and the like or other useful interventions.

In another preferred embodiment of the invention, the catheter body has a single central, lumen into which the four puller wires and the lead wires from the five lumen tip converge and travel, the full length of the body into the control handle. In this embodiment, the compression coils may be retained or omitted. Preferably, however, compression coils are included and the proximal ends, of each of two diametrically opposed pairs of compression coils are fixedly attached to the proximal end of the catheter body. The distal ends of the compression coils are fixedly attached to the distal end of the catheter body and/or at a selected location along the length of the catheter tip section. In a preferred embodiment where one diametrically opposed pair of compression coils extends into the catheter tip and the other pair is fixedly attached to the distal end of the catheter body, it is preferable that the pair of compression coils extending into the tip is fixedly attached at a location on the tip section where the distal end of the puller wires of the other opposed pair of compression coils are fixedly attached.

Longitudinal movement of the puller wires is accomplished by means of the control handle. A preferred control handle comprises a handle body having four movable, or slidable, members. Each slidable member is connected to a puller wire so that movement, preferably proximal movement, of a slidable member from a first position towards a second position results in proximal movement of the puller wire associated with that member with respect to the catheter body and deflection of the tip section in the direction of that puller wire quadrant. Preferably, means are provided to prevent simultaneous proximal movement of diametrically opposed buttons.

BRIEF DESCRIPTION OF THE DRAWINGS

These and other features and advantages of the present invention will be better understood by reference to the following detailed description when considered in conjunction with the accompanying drawings wherein:

FIG. 3 is a longitudinal cross-sectional view showing a preferred means for joining a catheter tip section to the catheter body.

FIG. 4 is a longitudinal cross-sectional view of the catheter tip section showing a preferred means for anchoring the puller wires.

FIG. 5a is a longitudinal cross-sectional view of a preferred puller wire T-bar anchor.

FIG. 5b is a longitudinal cross-sectional view of a preferred puller wire T-bar anchor of FIG. 5a rotated 90° to show the cross-piece on end.

FIGS. 6a and 6b are longitudinal cross-sectional views of the catheter tip section showing other preferred means for anchoring the puller wires.

FIG. 8 in a longitudinal cross-sectional view of a preferred control handle.

FIG. 9 is a transverse cross-sectional view of the control handle of FIG. 8 taken along line 9—9 without insert 79.

DETAILED DESCRIPTION

Figure 1:
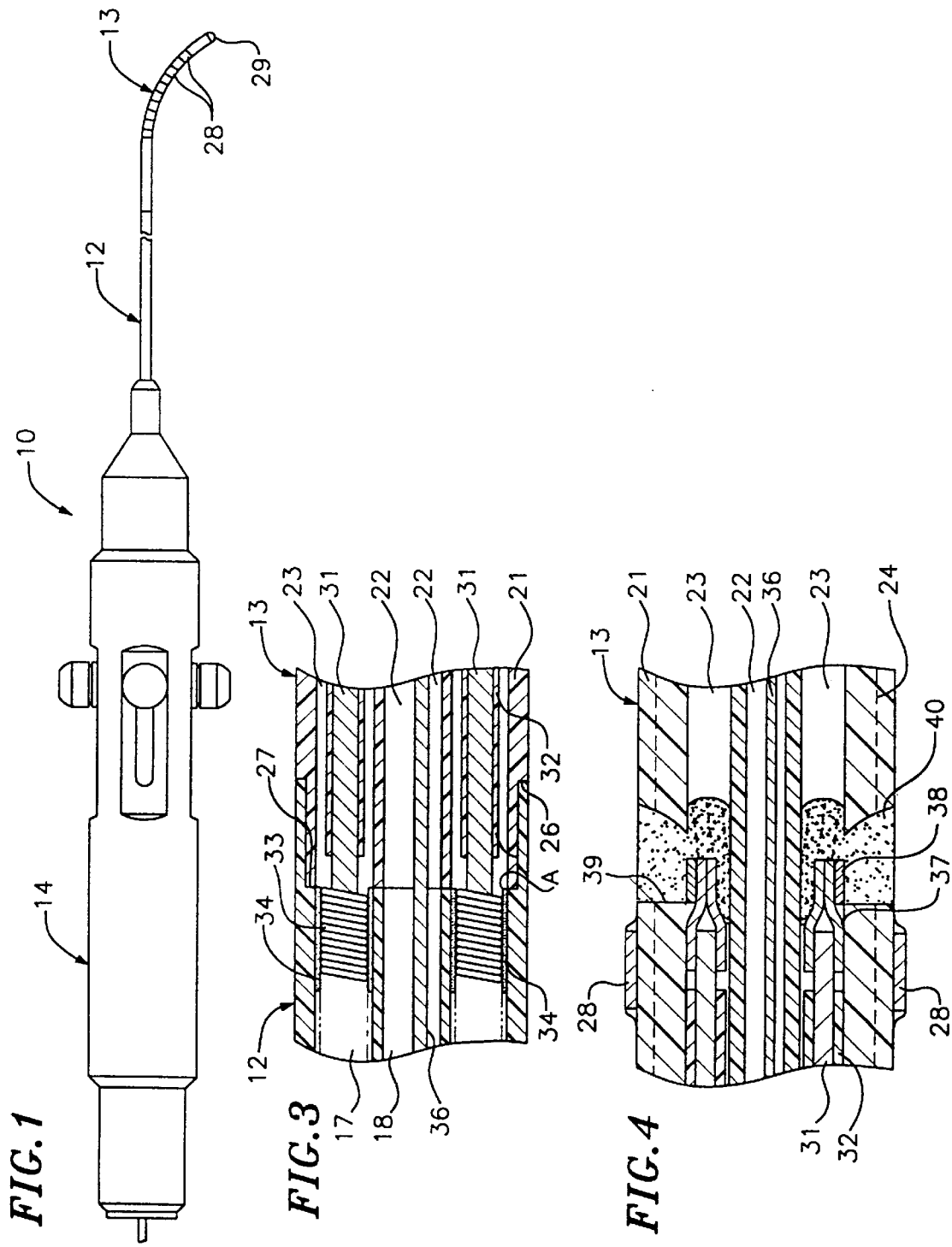
FIG. 1 is side view showing a preferred omni-directional catheter constructed in accordance with the present invention.

A particularly preferred deflectable electrode catheter constructed in accordance with the present invention as shown in FIGS. 1–10. In FIG. 1, the catheter 10 comprises an elongated catheter body 12, a deflectable tip section 13 and a control handle 14. In the embodiment shown, the tip section 13 carries a plurality of electrodes 28 and 29.

The overall length and diameter of the catheter may vary according to the application. A presently preferred catheter has an overall length of about 48 inches and an outer diameter of about 0.09 inches.

Figure 2:
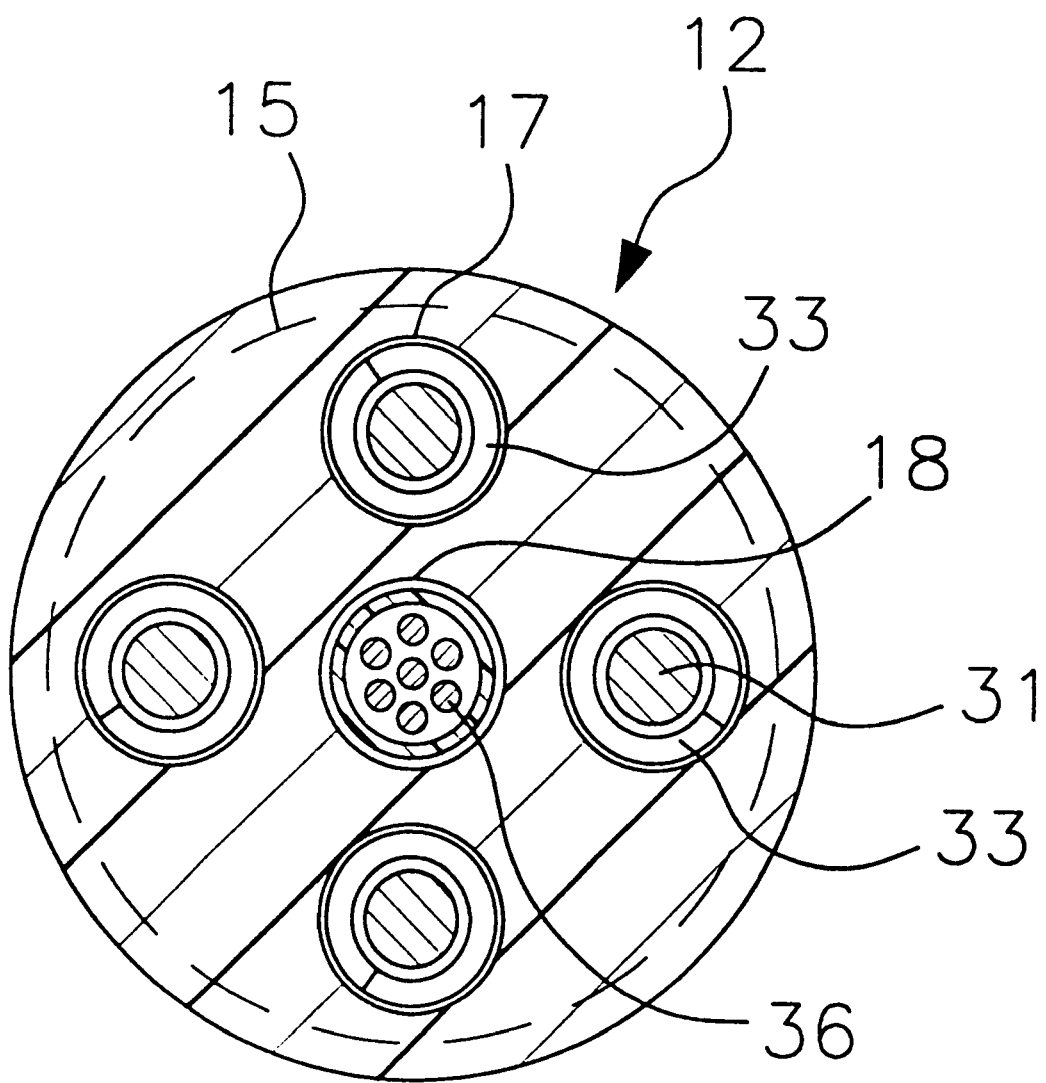
FIG. 2 is a transverse cross-sectional view of one embodiment of a catheter body showing the lumen arrangement.

With reference to FIG. 2, the catheter body 12 comprises an elongated tubular construction having four outer lumens 17 and a central lumen 18. The outer lumens 17 are arranged symmetrically into quadrants about the central lumen 18. The diameter of the lumens may vary as desired. In a preferred embodiment, each of the lumens has a diameter of about 0.018 inch. The catheter body 12 is made of any suitable non-toxic material such as polyurethane. The catheter body 12 is preferably reinforced with at least one layer of a braided mesh 15 of stainless steel or the like to increase its torsional stiffness.

With reference to FIG. 4, the catheter tip section 13 comprises a short section of flexible tubing 21 having a central lumen 22 and four outer lumens 23 positioned symmetrically about the central lumen 22 as in the catheter body 12. The tubing 21 is made of a suitable material and is preferably more flexible than the catheter body 12. A presently preferred material for the catheter tip section 13 is polyurethane. The catheter tip section 13 is preferably reinforced with a metallic braided mesh 24 similar to that on the catheter body 12 to impart the same high torque characteristics without appreciably increasing its bending stiffness.

The diameter of the catheter tip section 13 is preferably the same as or slightly smaller than that of the catheter body 12. In a preferred embodiment, the diameter of the catheter tip section is about 0.08–0.09 inches and the length is about 3 inches.

A preferred means for attaching the catheter tip section 13 to the catheter body 12 is illustrated in FIG. 3. The proximal end of the catheter tip section 13 comprises an outer circumferential notch 26 and the distal end of the catheter body 12 comprises an inner circumferential notch 27. The notches 26 and 27 are sized such that the proximal end of the catheter tip section 13 fits snugly into the distal end of the catheter body 12. The catheter tip section 13 is then fixedly attached to the catheter body by polyurethane glue or the like, creating a seam on the outer surface of the catheter at the junction between the catheter tip section 13 and the catheter body 12. The central lumen 22 and outer lumens 23 of the catheter tip section 13 are aligned with and communicate with the central lumen 18 and outer lumens 17 of the catheter body 12 respectively.

Along the length of the catheter tip section 13 are a plurality of ring electrodes 28. The length of the electrodes 28 is not critical but is preferably about one to four millimeters. The electrodes 28 are spaced apart a distance of about 2 to 4 millimeters. A tip electrode 29 is at the distal end of the tip section 13.

Each electrode 28 and 29 is connected to a separate lead wire 36 which extends through the central lumens 18 and 22.

The proximal ends of lead wires 36 are connected to an appropriate jack or other connector which can be plugged into or otherwise connected to a suitable monitor.

Each ring electrode 28 has an associated lead wire 36 which extends through the wall of the tip section to the electrode. Connection of the lead wires 36 to the electrode 28 is accomplished, for example, by first making a small hole through the wall of the catheter tip section 13 and into the central lumen 22. Such a hole may be created, for example, by inserting a needle through the tip section wall and heating the needle sufficiently to form a permanent hole. A lead wire 36 is then drawn through the hole by using a microhook or the like. The ends of the lead wire 36 are then stripped of any coating and soldered or welded to the underside of the electrode 28 which is then slid into position over the hole and fixed in place with polyurethane glue or the like.

A puller wire 31 extends from the control handle 14 through each of the outer lumens 17 in the catheter body 12 and into aligned outer lumen 23 of the tip section 13. The puller wire 31 is made of any suitable metal such as stainless steel or Nitinol and is coated with Teflon®, Kevlor, carbon fiber or the like. The puller wire has a diameter preferably from about 0.006 to about 0.010 inch.

With reference to FIG. 2, within the catheter body 12, there is provided a compression coil 33 extending through each outer lumen 17 in surrounding relation to each puller wire 31. The compression coil 33 is made of a suitable metal, e.g., stainless steel, which is tightly wound on itself to provide flexibility, i.e., bending, but to resist compression. The inner diameter of the compression coil 33 is selected to be slightly larger than the diameter of the puller wire 31. For example, when the puller wire 31 has a diameter of about 0.007 inch, a compression coil 33 having an inner diameter of about 0.008 inch is presently preferred. The outer diameter of the compression coil 33 is likewise slightly smaller than the diameter of the lumen 17 through which it extends. For example, if the outer lumen 17 has a diameter of about 0.018 inch, the compression coil 33 preferably has an outer diameter of about 0.017 inch.

The compression coil 33 is fixedly attached to the proximal and distal ends of the catheter body 12 by polyurethane glue or the like. The glue may be applied through a syringe or the like to the outer circumference of the ends of the compression coil 33, for example as shown in FIG. 3 as location A. Glue applied to this location wicks inwardly between the compression coil 33 and the wall forming the lumen 17. Upon curing, the glue joint 34 is formed. Alternatively, the glue may be applied by means of a syringe or the like through a hole between the outer surface of the catheter body 12 and the lumen 17. Such a hole may be formed for example by a needle or the like which punctures the catheter body wall and is heated sufficiently to form a permanent hole. The glue is introduced through the hole to the outer surface of the compression coil 33 and wicks around the outer circumference to form a glue joint 34 about the entire circumference of the compression coil 33.

If the latter method is used, it is understood that the distal end of the compression coil 33 could be located in the proximal portion of the catheter tip section 13 rather from at the distal end of the catheter body 12. Such an embodiment provides added support to the juncture of the catheter body 12 and catheter tip section 13. Each puller wire 31 is preferably coated with a very thin coating of Teflon®. This coating imparts lubricity to the puller wire 31 within the compression coil 33.

Each puller wire 31 is anchored to the side of the catheter tip section 13 or to a tip electrode. With reference to FIGS. 4 and 5, within the tip section 13 the Teflon® sheath 32 prevents the puller wire from cutting into the wall of the tip section 13 when the tip section 13 is deflected. At its distal end, the puller wire 31 extends beyond the Teflon® sheath 32. The Teflon® coating on the puller wire 31 may also be removed at the distal end of the puller wire 31 or left on under the anchor 35. An anchor 35 is fixedly attached to the distal end of the puller wire 31. In a preferred embodiment, the anchor is formed by a metal tube 37, e.g., a short segment of hypodermic stock, which is fixedly attached, e.g., by crimping, to the distal end of the puller wire. The tube 37 has a section which extends a short distance beyond the distal end of the puller wire 31. A cross-piece 38 made of a small section of stainless steel ribbon or the like is soldered or welded in a transverse arrangement to the distal end of the tube section 37 which is flattened during the operation. This creates a T-bar anchor 35. A notch 39 is created in the side of the catheter tip section 13 resulting in an opening into the outer lumen 23. The anchor 35 lies particularly within the notch 39. Because the length of the ribbon forming the cross-piece 38 is longer than the diameter of the opening into the lumen 23, the anchor cannot be pulled completely into the lumen 23. The notch 39 is then sealed with polyurethane 40 or the like to give a smooth outer surface.

In a preferred embodiment, the puller wires 31 are divided into two pairs, a first pair being anchored proximal to the anchor location of the second pair. The second pair is anchored to the wall of the tip section 13 adjacent the distal end of tip section 13 or to a tip electrode. The first pair of puller wires 31 are anchored to the wall of the tip section at a location spaced apart proximally from the anchor sites of the second pair. In such an arrangement, the first pair may be anchored to the side wall of the tip section 13 as described above or, alternatively, may be anchored at the distal end of the tip section 13 as shown in FIG. 6A. In this arrangement, the puller wire 31 extends to the distal end of the outer lumen with the anchor, which is attached to the end of the puller wire, lying beyond the end of the lumen 23. The anchor 35 is fixed in this position by a polyurethane cap 41 which also seals the distal end of the catheter tip section 13. Because the cross-piece is longer than the diameter of the lumen 23 the anchor 35 cannot be pulled back into the lumen when the tip section 13 is deflected. This alternative anchoring method is useful when there is no tip electrode 29. If a tip electrode 29 is present, the puller wires 31 may be anchored to the side wall of the tip section 13 or to the tip electrode 29, e.g., by solder, as shown in FIG. 6B.

Figure 7:
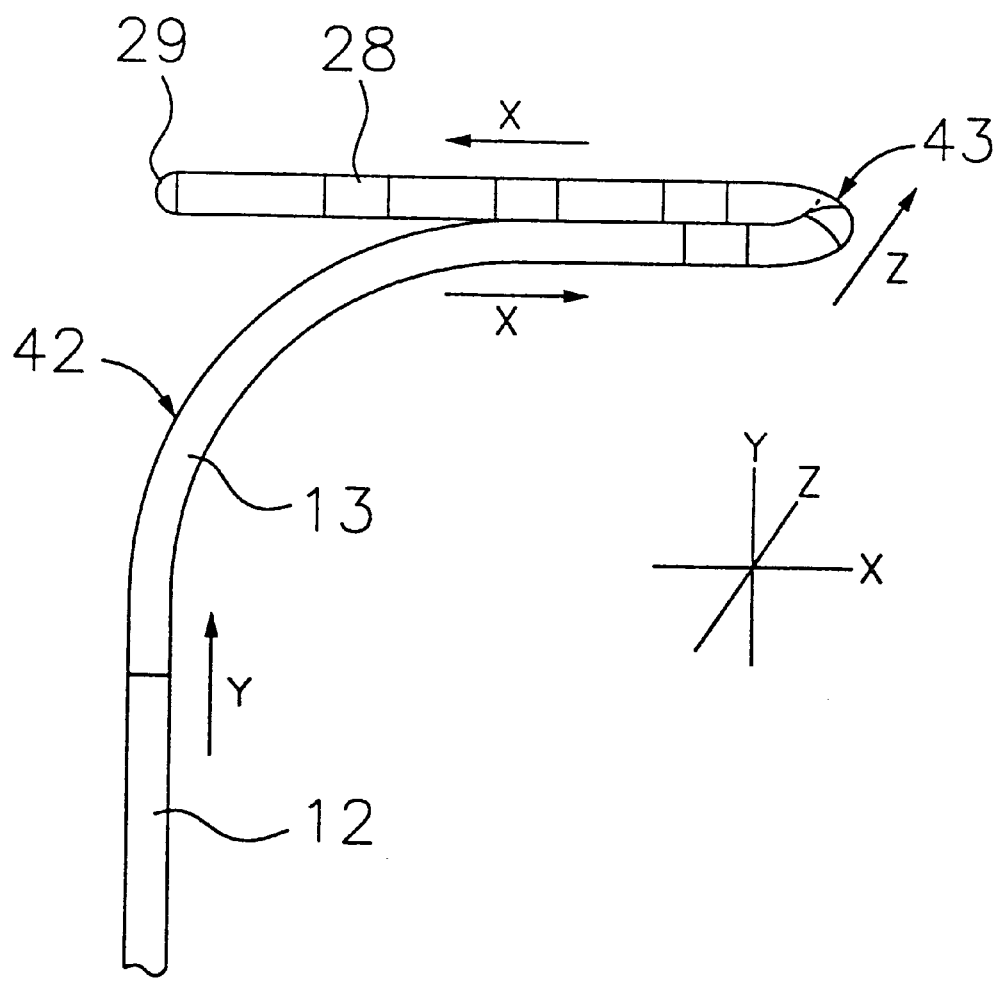
FIG. 7 is a perspective view of a tip section deflected into a compound curve.

The distance between the distal end of the compression coil 33 and the anchor sites of the puller wire 31 in the tip section 13 determines the curvature of the tip section 13 in the direction of that puller wire 31. For example, the arrangement of the anchor sites of the puller wires 31 described above, i.e., two diametrically opposed pairs anchored at different distances from the distal end of the compression coil 33, allows a long reach curve in a first plane and a short reach curve in a plane 90° from the first, i.e., a first curve in one plane generally along the axis of the catheter tip section before it is deflected, and a second curve distal to the first curve in a plane transverse, and preferably normal to the first plane. The high torque characteristic of the catheter tip section 13 reduces the tendency for the deflection in one quadrant to deform the deflection in the adjacent quadrant. Such a compound curve is shown in FIG. 7. This tendency may be flirter reduced and even eliminated by locating the distal ends of the second opposing pair of compression coils distal to the distal ends of the first opposing pair of compression coils, preferably at a location adjacent the anchor sites of the first opposing pair of puller wires. Such a capability allows a physician to deflect the tip section 13 in a first direction to bring the distal tip near a desired site on the heart wall and then deflects the distal portion of the tip section from side to side, i.e., transverse to the first deflection, to reach around an obstruction such as a papillary muscle or chords It is understood that each of the four puller wires 31 may be anchored at the same location along the length of the catheter tip section 13 in which case the curvatures of the tip section 13 in all directions are the same and the tip section 13 can be made to deflect in any direction without rotation of the catheter body 12. Alternatively, the puller wires 31 may be anchored at three or four different locations. In the latter case, each quadrant has a distinct curvature. By rotating the catheter body 12, which is possible due to the high torque shaft, a physician may use any of the four curvatures or combinations thereof as desired.

Figure 10:
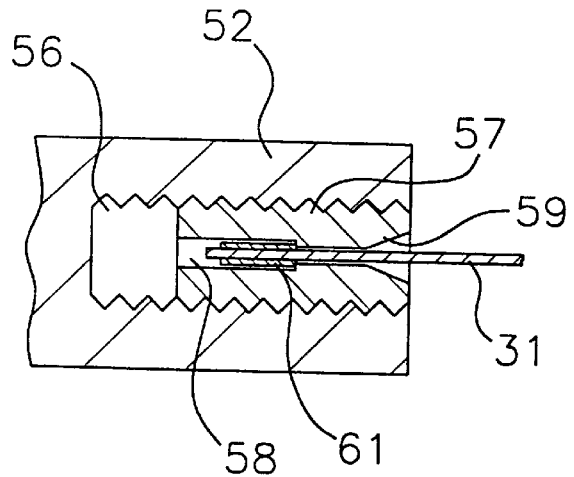
FIG. 10 is a transverse cross-sectional view of a preferred means for securing the puller wire to the control handle.

Longitudinal movement of the puller wires is controlled by control handle 14. With reference to FIGS. 8–10, the control handle 14 comprises a generally cylindrical body 45, a distal cap 46 at the distal end of the control handle body 45 and a proximal cap 47 at its proximal end. The cylindrical body 45 comprises a central cylindrical lumen 48 and four outer cylindrical lumens 49 which overlap with and hence communicate with the central lumen 48. At its distal end, the cylindrical body 45 comprises a cylindrical flange 51. A piston 52, comprising a movable member, is slidably mounted within each of the outer lumens 49 in the control handle 14. The piston 52 is generally cylindrical along about two-thirds of its length. The proximal third of the piston is generally semicircular in cross-section having a flat surface 53 facing the axis of the control handle. At the transition between the distal cylindrical portion and the proximal semi-cylindrical portion of the piston, there is an angled, generally flat face 54. A preferred angle is about 45°.

With reference to FIG. 10, at the distal end of the piston 52, there is a threaded axial hole 56 which receives a threaded set screw 57. The set screw has an axial bore 58 therethrough for passage of the proximal end of the puller wire 31. In a preferred embodiment, the axial bore 58 has a distal section with a diameter slightly larger than the diameter of the puller wire 31 and a proximal section having a diameter larger than that of the distal section. The entrance 59 to the axial bore is beveled.

The puller wire 31 extends through the axial bore 58 of the set screw 57 and is anchored thereto. A preferred means for anchoring the puller wire 31 to the set screw 57 as shown in FIG. 10 comprises a short piece of hypodermic stock 61 which is fixedly attached, i.e., by crimping, to the proximal end of the puller wire 31 after it has passed through the distal section of the axial bore 58 of the set screw 57. The hypodermic stock 61 has a diameter greater than the diameter of the distal section of the axial bore 58 and prevents the puller wire from being pulled through the set screw 52. As an alternative, a cross-member, e.g., stainless steel ribbon, may be welded to the proximal end of the puller wire such that the cross-member prevents the puller wire from being pulled through the axial bore of the set screw.

It is understood that any mechanism for attaching the proximal end of the puller wire to the piston may be used.

Along the length of each piston 52, there is provided a threaded, radial hole 62 into which a threaded post 63 is screwed. The post 63 extends radially outwardly from the axis of the control handle 14 through a longitudinal slot 64 in the control handle body. At the end of the post 63, remote from the piston 52, there is fixedly attached a button 65. This configuration completes a functional moveable member. In this arrangement, the movable member is slidably adjustable between two positions defined by the length of the slot 64. An operator may grip the outer surface of the control handle body 45 and slide the button 65 and piston 52 longitudinally the length of the slot 64 by means of thumb pressure. In a particularly preferred embodiment, the buttons 65 are differentiated, e.g., by size, texture, etc., e.g., as shown in FIG. 9 to provide a tactile identification of the puller wire 31 which is being manipulated. For example, in the embodiment described above involving two diametrically opposed pairs of puller wires 31, each pair anchored at different sites along the length of the tip section, the buttons 65 associated with one puller wire pair may be knurled and the buttons associated with the other puller wire pair may be smooth This avoids any confusion by a physician in manipulating the catheter during a medical procedure.

In a preferred embodiment, there is provided means for adjusting the amount of manual pressure required to slide a button 65 along the length of the slot 64. For example, one physician may desire a control handle having a "light touch," i.e., requiring only a small amount of pressure to slide the buttons 64 and hence making deflection off the tip section 13 very responsive to the physician's touch. Another may prefer that the handle 14 require substantial pressure to slide the buttons 65 so that the tip curvature will remain when the button 65 is released With reference to FIG. 8, a preferred button arrangement comprises a washer 71 and an O-ring 72 positioned between the button 65 and the body 45 of the control handle 14 and a compression spring 70 in surrounding relation to the post 63 between the button 65 and the washer 71. In this arrangement, rotation of the button 65 in one direction causes the post 63 to thread into the radial hole 62 of the piston 52 which increases the spring force and O-ring force pressing the washer 71 against the control handle body 45. This increases the amount of frictional force that must be overcome to slide the button 65 along the length of the slot 64. Rotation of the button 65 in the opposite direction lessens such forces.

The combination of spring 70 and O-ring 72 cause the button 65 not to rotate during use and therefore, the friction force setting to remain locked once set. By the choice of spring 70, O-ring 72 and thread pitch, the resolution of the friction setting mechanism may be varied as desired.

The distal cap 46 comprises a cylindrical portion 73 having a circumferential notch 74 at its proximal end. The circumferential notch mates with the cylindrical flange 51 of the control handle body 45. That is, the outer diameter of the notch 74 is about the same as the inner diameter of the flange 51 of the control handle body 45. The distal cap 46 is then press fit into the control handle body 45 until the distal edge of the flange 51 engages a shoulder 75 of the cap 46. Above the cylindrical portion, the distal cap 46 comprises a generally conical portion 76. A small extension 77 projects distally at the top of the conical section 76. The projection 77 comprises an axial hole through which the catheter body 12 extends and is fixedly attached thereto, e.g., by glue or the like.

Each of the puller wires 31 passes out of the proximal end of the catheter body 12 and extends through the distal cap 46 of the control handle 14 to a separate piston 52 within the control handle body 45. The proximal ends of the puller wires 31 are fixed to the pistons 52, e.g., by means of the set screws 57 described above. In this arrangement, longitudinal movement of a piston 52 by means of pressure on the associated button 65 results in longitudinal movement of the puller wire 31 associated with that piston 52 and deflection of the tip section 13 in the direction of that puller wire quadrant.

To assure that the puller wires 31 transition smoothly from the catheter body 12 to their anchor sites on the pistons 52, puller wires 31 exit the cap 46 around a radius and then around another radius before entering the piston 52. The first radius is a flaring of the hole in the cap 46. The second radius is formed by an insert 79 which seats into the distal end of the central lumen 48 of the control handle 14. The insert 79 comprises a rounded head portion having an outer surface adjacent the distal ends of the pistons 52. The puller wires 31 pass from the catheter body 12 around the head portion of the insert 79 and then to the pistons. The rounded head of the insert 79 assures that the puller wires 31 are generally co-axial with the pistons 52 at their points of attachment. This, in turn, avoids any sharp bends in the puller wires 31 at the points of attachment which could lead to weakening and potential breakage.

To prevent simultaneous movement of diametrically opposed puller wires 31 and yet allow for simultaneous movement of any two adjacent puller wires, there is provided a movable stop 81 within the handle. The stop comprises a central post 82 extending distally from the proximal cap 47 to a point adjacent the angled faces 54 of the pistons 52. At the distal end of the post 82, there is an enlarged head 83 having a conical surface 84 similarly angled to the face 54 of the pistons 52. The post 82 comprises an axial bore through which the electrode lead wires 36 may pass.

When one piston is moved proximally, the angled face 54 of that piston 52 engages the conical surface 84 of the head 83 of the stop 81 causing the post 82 and head 83 to move off axis. If one attempts to move the diametrically opposed piston 52 proximally, the conical surface 84 of the head 83 will engage the angled face 54 surface of that piston 52 and prevent proximal movement This is because, by virtue of the position of the first piston, the post 82 and head 83 cannot move out of the way of the second piston. Thus, the stop 81 allows only one piston of each pair of diametrically opposed pistons to be moved at one time.

In the embodiment described above, the central lumen 18 is used for passage of electrode lead wires 36. It is understood that the central lumen may be omitted, if desired. In such an embodiment, one or more off-axis lumens 17 must be sufficiently large to carry the electrode lead wires 36 in addition to the compression coil 33 and the puller wire 31. A preferred method for providing a lumen which carries a compression coil in surrounding relation to a puller wire and one or more electrode lead wires is described in U.S. Patent Application No. 5,827,278 the disclosure of which is incorporated herein by reference. In such an embodiment, the compression coil is preferably covered by a non-conductive sheath to prevent electrical contact with the lead wires. Moreover, a tunnel must be formed in each of the glue joints securing the proximal and distal ends of the compression coil to the catheter body. The tunnels provide means for passage of the electrode lead wires through the glue joints. Such a tunnel may be formed, for example, by short pieces of polyimide tubing or the like.

Alternatively, if the lead wires 36 are carried in one or more of the off-axis lumens, the central lumen may be used as a delivery route for fluids, solids, devices, and the like (e.g., pharmaceutical compounds, growth factors, hormones, gene therapy vectors, angiography tracer substances, or angioplasty devices), or as a means for collecting tissue or fluid samples.

In another particularly preferred embodiment of the invention, the catheter body comprises a single central or axial lumen rather than multiple off-axis lumens. The catheter 10 is as described above with reference to FIG. 1 in its external features. In this preferred embodiment, shown in FIG. 11, the catheter body 12 comprises a single central lumen 90 through which four puller wires 31 extend. The catheter body may be made of any suitable material and preferably comprises an outer polyurethane wall 91 containing a braided stainless steel mesh and an inner stiffening tube 92, the interior of which forms the central lumen 90. The stiffening tube 92 may be made of any suitable material such as nylon or polyimide. Polyimide is presently preferred as the same degree of stiffness can be obtained with a thinner-walled tubing.

Figure 12:
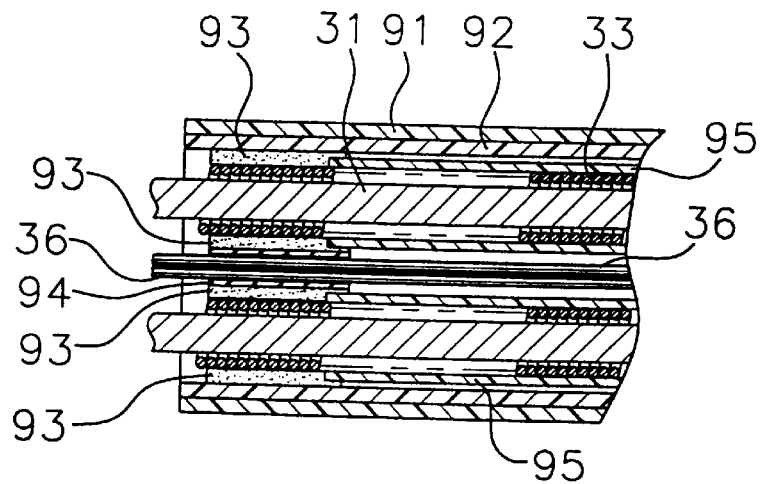
FIG. 12 is a longitudinal cross-sectional view of the proximal end of the catheter body of FIG. 11.
Figure 13:
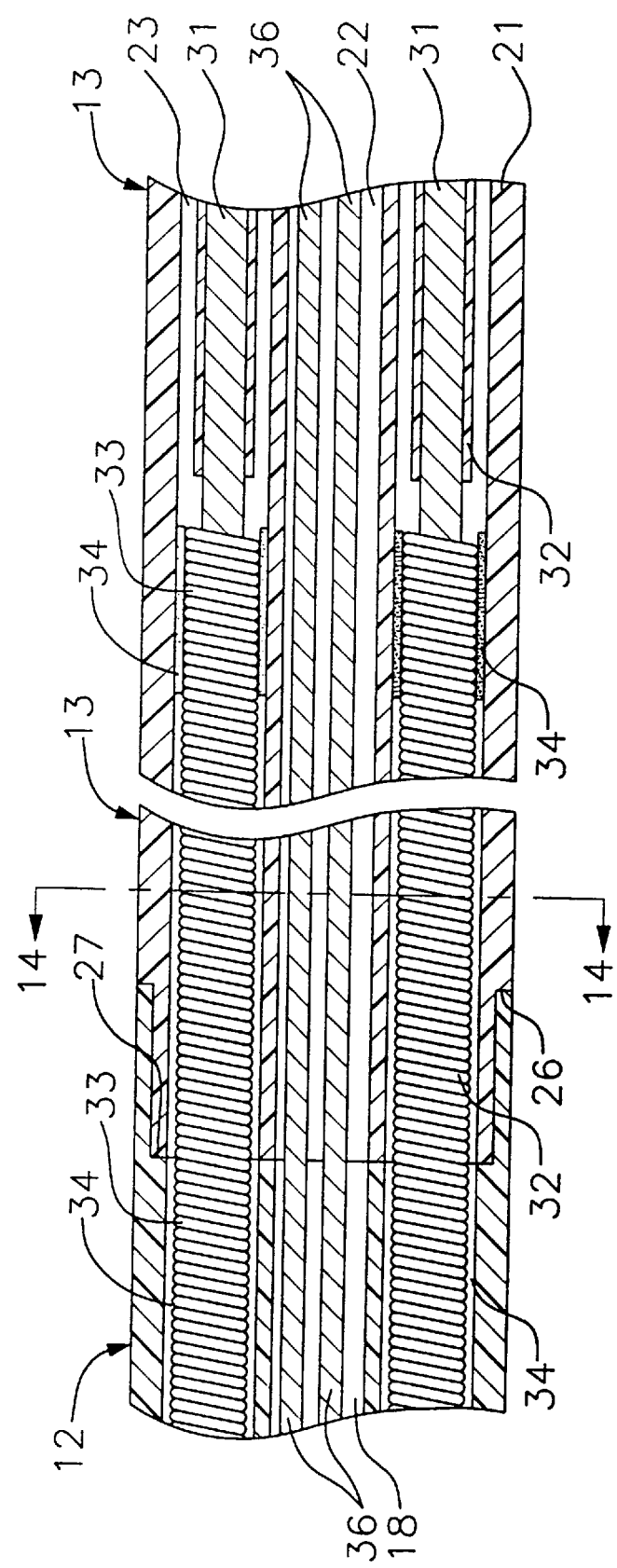
FIG. 13 is longitudinal cross-sectional view of a preferred means of joining a catheter body to the deflectable catheter tip and of attaching compression coils to the deflectable tip.
Figure 14:
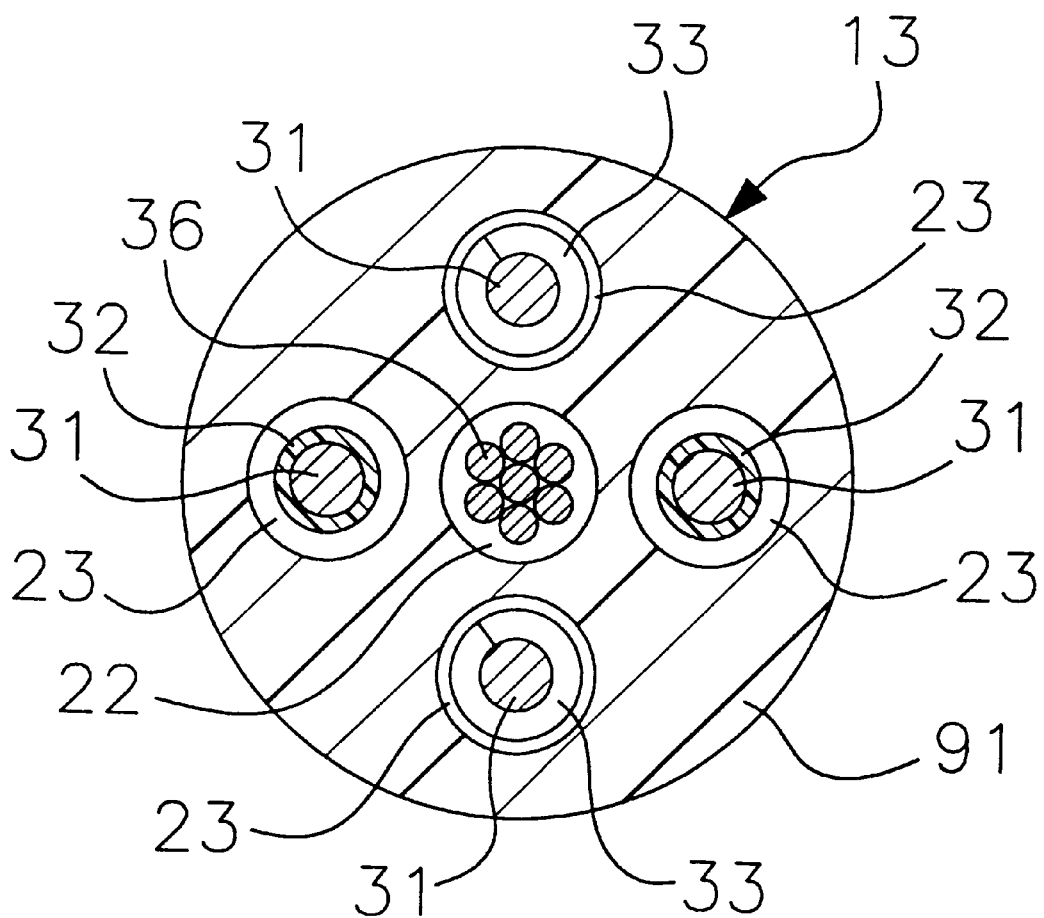
FIG. 14 is a transverse cross-sectional view of the tip section of FIG. 13 taken along line 14—14.

A compression coil 33 surrounds each puller wire 31 as described above. The compression coils are fixedly attached at the proximal ends of the catheter body. At the distal ends of the catheter body 12, at least one opposed pair of compression coils is fixedly attached to the catheter body by means of polyurethane glue joints 93 or the like as shown in FIG. 12. A tunnel 94 is provided through the glue joint for passage of the electrode lead wires. Preferred tunnels are formed by short pieces of non-conductive tubing, preferably polyimide tubing, for example as described in Webster, Jr.

application filed May 20, 1997. In a preferred embodiment, shown in FIGS. 13 and 14, at least one opposed pair of compression coils extends past the junction of the catheter body 12 and the catheter tip 13 into the catheter tip, where the compression coils 33 are fixedly attached at a selected location along the length of the catheter tip by means of glue joints 34. Preferably one opposing pair of compression coils are fixedly attached along the length of the tip section at one location and the other opposing pair of compression coils are fixed along the length of the tip section at a second location distal to the first location. In a particularly preferred embodiment, the second location is where the distal ends of the first pair of puller wires 36 are attached to the wall of the tip section. This configuration permits a first curve in one direction by one of the first pair of puller wires unaffected by the second puller wires and a second curve distal to the first curve in a direction 90° to the first curve unaffected by the first puller wire. Combined with the superior torsional characteristics, this embodiment allows the physician to steer the catheter in any direction and achieve a desired compound curve due to the stiffness afforded by the compression coils in the catheter body.

Figure 11:
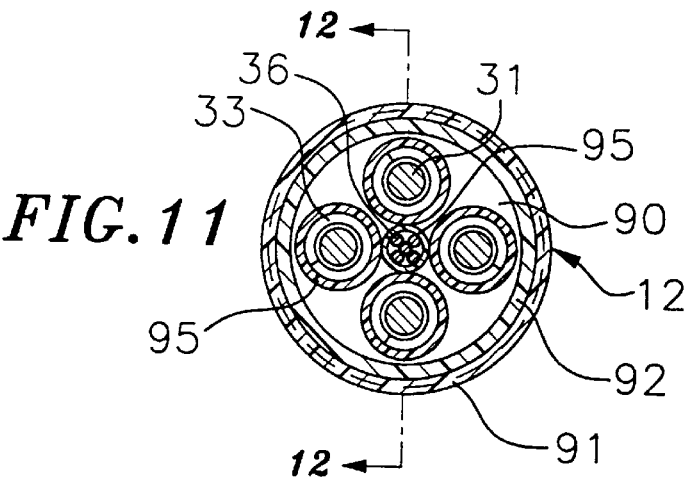
FIG. 11 is a transverse cross-sectional view of a presently preferred catheter body construction.

In the embodiment shown in FIG. 12, the tunnels 94 are formed centrally of the compression coils 33. It is understood that the tunnel 94 could be formed at a location between the compression coils 33 and the wall of the lumen 90 if desired. Between the glue joints 93, the compression coils 33 are covered by a non-conductive sheath 95, preferably polyimide tubing. The presence of the sheath 95 around the compression coils 33 is preferred to prevent electrical contact between the electrode lead wires 36 and the compression coils 33 in the catheter body's single lumen. Preferably, the lead wires 36 are also encased in a non-conductive sheath 95, e.g., of polyimide tubing as shown in FIG. 11.

The catheter tip section 13 is as described above, with four off-axis lumens. In the tip section, the puller wires branch into separate off-axis lumens and are anchored to the walls of the tip sections as described above. Likewise, the proximal ends of the puller wires are attached to a control handle, for example as described above.

In the latter preferred embodiment, it is understood that, rather than compression coils, the puller wires may extend through stiff nylon tubes or the like. Further, if the puller wires are maintained close to the axis of the catheter body, the compression coils (or nylon tubes or the like) through which the puller wires extend in the above embodiments may be omitted altogether.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A control handle for a steerable catheter comprising:
    a housing comprising an outer wall, a hollow interior and a longitudinal slot through the outer wall into the interior;
    a piston movable longitudinally within the interior of the housing;
    a button mounted exterior to the housing connected to the piston through the longitudinal slot, said button being movable along the length of the slot in response to manual pressure on the button whereby movement of the button along the length of the slot results in longitudinal movement of the piston; and
    means for adjusting the amount of pressure required to move the button along the length of the slot.

2. A control handle as claimed in claim 1 wherein the button is connected to the piston by a post which extends through the slot between the button and piston and wherein the means for adjusting the amount of pressure required to move the button along the length of the slot comprises a spring disposed around the post between the button and the exterior of the housing for applying a biasing force against the button and housing and means for adjusting the biasing force of the spring against the button and housing.

3. A control handle as claimed in claim 2 wherein the means for adjusting the biasing force of the spring against the button and housing comprises screw threads on at least one end of the post which screw into a threaded hole in one of the piston and button whereby rotation of the button in one direction causes the post to screw into the threaded hole, decreasing the distance between the button and piston and increasing the biasing force of the spring against the button and housing and rotation of the button in the opposite direction causes the post to unscrew from the threaded hole increasing the distance between the button and piston and decreasing the biasing force of the spring against the button and housing.

4. A control handle as claimed in claim 1 wherein the button is connected to the piston by a post which extends through the slot between the button and piston and wherein the means for adjusting the amount of pressure required to move the button along the length of the slot comprises an O-ring disposed around the post between the button and exterior of the housing and means for adjusting the biasing force of the O-ring against the button and housing.

5. A control handle as claimed in claim 4 wherein the means for adjusting the biasing force of the O-ring against the button and housing comprises screw threads on at least one end of the post which screw into a threaded hole in one of the piston and button whereby rotation of the button in one direction causes the post to screw into the threaded hole, decreasing the distance between the button and piston and increasing the biasing force of the O-ring against the button and housing and rotation of the button in the opposite direction causes the post to unscrew from the threaded hole increasing the distance between the button and piston and decreasing the biasing force of the O-ring against the button and housing.

6. A control handle for a steerable catheter comprising:
    a housing comprising an outer wall, and a hollow interior,
    at least one pair of opposing pistons each connectable to a puller wire, said pistons being movable longitudinally within the housing;
    means for longitudinally moving each piston within the housing; and
    means for preventing simultaneous longitudinal movement of both opposing piston.

7. A control handle as claimed in claim 6 wherein the housing further comprises a pair of longitudinal slots on opposing sides of the outer wall and each piston is associated with a longitudinal slot;
    the means for longitudinally moving each piston within the housing comprises at button mounted exterior to the housing connected to the piston through the longitudinal slot, said button being movable along the length of the slot in response to manual pressure on the button whereby movement of the button along the length of the slot results in longitudinal movement of the piston; and the means for preventing simultaneous longitudinal movement of both opposing pistons comprises a stop movable between a first position permitting longitudinal movement of one of the opposing pistons and a second position preventing longitudinal movement of one of the opposing pistons.

8. A control handle as claimed in claim 7 wherein longitudinal movement of one opposing piston causes the stop to move from its first position to a second position preventing longitudinal movement of the other opposing piston.

9. A control handle for a steerable catheter comprising:

a housing having a central axis and four off-axis lumens, forming two pairs of diametrically-opposed lumens; and four movable members, each member being associated with and slidable within a different off-axis lumen in the housing, each movable member being movable between first and second positions relative to the housing.

10. A control handle as claimed in claim 9, wherein the four off-axis lumens are arranged symmetrically about the central axis of the housing.

11. A control handle as claimed in claim 9, wherein the housing further comprises an axial lumen.

12. A control handle as claimed in claim 9, further comprising means for preventing simultaneous longitudinal movement of the moveable members in diametrically-opposed lumens.

13. A control handle as claimed in claim 9, wherein the means for preventing simultaneous longitudinal movement of movable members in diametrically-opposed lumens comprises a stop movable between a first position permitting longitudinal movement of one of the members and a second position preventing longitudinal movement of the other member.

* * * * *

UNITED STATES PATENT AND TRADEMARK OFFICE
CERTIFICATE OF CORRECTION

PATENT NO.    : 6,066,125
DATED         : May 23, 2000
INVENTOR(S)   : Wilton W. Webster, Jr.

It is certified that error appears in the above-identified patent and that said Letters Patent is hereby corrected as shown below:

Column 12,
Line 61, replace "piston" with -- pistons --
Line 67, replace "comprises at" with -- comprises a --

Signed and Sealed this

Tenth Day of December, 2002

JAMES E. ROGAN
*Director of the United States Patent and Trademark Office*